US011273275B2

United States Patent
Romano et al.

(10) Patent No.: US 11,273,275 B2
(45) Date of Patent: Mar. 15, 2022

(54) AUTO-ADJUSTMENT OF PATIENT EXPIRATORY PRESSURE

(71) Applicant: KONINKLIJKE PHILIPS N.V., Eindhoven (NL)

(72) Inventors: Robert Romano, Pittsburgh, PA (US); Peter Douglas Hill, Murrysville, PA (US)

(73) Assignee: Koninklijke Phillips N.V., Eindhoven (NL)

(*) Notice: Subject to any disclaimer, the term of this patent is extended or adjusted under 35 U.S.C. 154(b) by 376 days.

(21) Appl. No.: 16/341,468

(22) PCT Filed: Oct. 9, 2017

(86) PCT No.: PCT/EP2017/075582
§ 371 (c)(1),
(2) Date: Apr. 12, 2019

(87) PCT Pub. No.: WO2018/069198
PCT Pub. Date: Apr. 19, 2018

(65) Prior Publication Data
US 2019/0290869 A1    Sep. 26, 2019

Related U.S. Application Data

(60) Provisional application No. 62/407,582, filed on Oct. 13, 2016.

(51) Int. Cl.
*A61M 16/00* (2006.01)
*A61M 16/06* (2006.01)

(52) U.S. Cl.
CPC ...... *A61M 16/024* (2017.08); *A61M 16/0069* (2014.02); *A61M 16/06* (2013.01);
(Continued)

(58) Field of Classification Search
CPC ............ A61M 16/021; A61M 16/022; A61M 16/024; A61M 16/026; A61M 16/0069; A61M 16/0057
See application file for complete search history.

(56) References Cited

U.S. PATENT DOCUMENTS 5,918,597 A    7/1999  Jones
6,588,422 B1*  7/2003  Berthon-Jones ...... A61M 16/00
                                        128/204.23
(Continued)

FOREIGN PATENT DOCUMENTS

EP    2245985 A1    3/2010
WO    2008031822 A1    3/2008
(Continued)

OTHER PUBLICATIONS

John J. Marini., "Dynamic Hyperinflation and Auto-Positive End-Expiratory Pressure: Lessons Learned over 30 Years", American Journal of Respiratory and Critical Care Medicine., vol. 184, No. 7, Oct. 1, 2011 (Oct. 1, 2011), pp. 756-762, XP055434633.
(Continued)

*Primary Examiner* — Margaret M Luarca
(74) *Attorney, Agent, or Firm* — Daniel H. Brean

(57) ABSTRACT

A system for adjusting extrinsic positive end expiratory pressure during an expiratory phase of a ventilator is provided. The system includes a computer system that comprises one or more physical processors programmed with computer program instructions which, when executed cause the computer system to: determine a respiratory reactance from airway flow information of the patient and airway pressure information of the patient, the airway flow information and airway pressure information of the patient being obtained from one or more sensors, and adjust the extrinsic positive end expiratory pressure during the expiratory phase
(Continued)

of the ventilator such that the determined respiratory reactance falls within a defined respiratory reactance range.

15 Claims, 7 Drawing Sheets

(52) U.S. Cl.
CPC ............ *A61M 2016/0027* (2013.01); *A61M 2016/0042* (2013.01); *A61M 2205/3344* (2013.01); *A61M 2230/40* (2013.01)

(56) References Cited

U.S. PATENT DOCUMENTS

| | | | | |
|---|---|---|---|---|
| 2010/0275921 A1* | 11/2010 | Schindhelm | ......... | A61B 5/7275 128/204.23 |
| 2012/0000468 A1 | 1/2012 | Milne | | |
| 2012/0125336 A1 | 5/2012 | Berthon-Jones | | |
| 2012/0266882 A1 | 10/2012 | Dellaca | | |
| 2013/0163740 A1 | 6/2013 | Noel | | |
| 2015/0045687 A1 | 2/2015 | Nakai | | |

FOREIGN PATENT DOCUMENTS

| | | |
|---|---|---|
| WO | WO2012127358 A1 | 9/2012 |
| WO | 2013163740 A1 | 11/2013 |
| WO | WO2016079703 A1 | 5/2016 |

OTHER PUBLICATIONS

David W. Kaczka et al., "Oscillation Mechanics of the Respiratory System: Applications to Lung Disease", Critical Reviews(TM) in Biomedical Engineering, vol. 39, No. 4, Jan. 1, 2011 (Jan. 1, 2011), pp. 337-359, XP055157519.

\* cited by examiner

AUTO-ADJUSTMENT OF PATIENT EXPIRATORY PRESSURE

CROSS-REFERENCE TO RELATED APPLICATIONS

This patent application claims the priority benefit under 35 U.S.C. § 371 of international patent application no. PCT/EP2017/075582, filed Oct. 9, 2017, which claims the priority benefit under 35 U.S.C. § 119(e) of U.S. Provisional Application No. 62/407,582, filed on Oct. 13, 2016, the contents of which are herein incorporated by reference.

BACKGROUND OF THE INVENTION

1. Field of the Invention

The present disclosure pertains to a method and a system for delivering a respiratory therapy to a patient, and, more particularly, to adjusting the expiratory pressure during an expiratory phase of such a system.

2. Description of the Related Art

A ventilation system or ventilator delivers respiratory therapy to a patient by delivering a gas to the patient's pulmonary system at a level above ambient pressure during inspiration. The ventilator has a number of options to control the expiratory pressure based on the patient's ventilatory requirements during the expiration or expiratory phase. For example, in the case of a patient having an expiratory flow limitation (EFL), the expiratory pressure (or extrinsic Positive End Expiratory Pressure or $PEEP_{ext}$) is set at, or near, a level of the patient's intrinsic PEEP in order to splint or hold open their lower airways to reduce air trapping and hyperinflation. The $PEEP_{ext}$ is Positive End Expiratory Pressure applied by the ventilator, while the intrinsic Positive End Expiratory Pressure is Positive End Expiratory Pressure caused by an incomplete exhalation.

An accurate measure of the degree of a person's EFL can be determined from an analysis of respiratory reactance signal, thus enabling the ventilator system to adjust the $PEEP_{ext}$ level to an optimal setting. However, the $PEEP_{ext}$ level could change significantly during the duration of expiration. Current solutions for setting the $PEEP_{ext}$ do not account for this change. Therefore, the current solutions either deliver therapy that, if the $PEEP_{ext}$ level set too high, will detrimentally increase a patient's hyperinflation and cause discomfort, or deliver therapy that, if the $PEEP_{ext}$ level set too low, will provide inadequate therapy. But, even within the portion of the patient's expiratory phase, the $PEEP_{ext}$ level required to provide an optimal therapy to a patient can vary and delivering a fixed level of $PEEP_{ext}$ could cause discomfort and adversely affect cardiac performance.

Also, ventilation systems that have the ability to deliver therapy with bi-level pressure support do so using numerous techniques for controlling an amplitude and waveform profile of the pressure, and therefore flow of gas to a patient's pulmonary system. For example, U.S. Patent Application No. US 2012/0125336 ("the '336 Publication) discloses a waveform that is a function of time and/or a phase in a respiratory cycle. The '336 Publication discloses that the pressure is a function of at least a waveform, an amplitude, and a smoothness parameter.

FIG. 4 shows a graphical illustration of the $PEEP_{ext}$ level being maintained constant during the expiratory phase in accordance with the prior art. For example, the $PEEP_{ext}$ (in FIG. 4) level was set to 8 $cmH_2O$ to eliminate on average the EFL during the expiration phase. The graph in FIG. 4 shows the EFL treated with optimized $PEEP_{ext}$.

FIG. 4 shows patient pressure on the left hand side Y-axis of the graph.

For example, the patient pressure is measured at a patient interface (e.g., a mask) and is measured in units of $cmH_2O$. FIG. 4 also shows respiratory reactance on the right hand side Y-axis of the graph, which is measured in $cmH_2O*s/L$. FIG. 4 also shows time on the X-axis of the graph, which is measured in seconds.

The top graph in FIG. 4 is an illustration of the patient pressure information and the bottom graph in FIG. 4 is an illustration of the respiratory impedance or respiratory reactance.

As shown in FIG. 4, during the early or first part (e.g., between 1.9 and 3.5 seconds) of the expiratory phase, the respiratory reactance, Xrs, is outside of the desired "reactance pattern" or range indicating that the $PEEP_{ext}$ level is too low (i.e., Xrs<the reactance pattern or range) during that condition. The desired reactance range is shown in FIG. 4. For example, the box labelled "Reactance Pattern" in FIG. 4 is desired reactance range.

Conversely, the respiratory reactance, Xrs is above the desired "reactance pattern" or range during the latter part (e.g., between 4 and 5.4 seconds) of the expiration indicating that the $PEEP_{ext}$ level is too high (Xrs>reactance pattern or range) during that condition. The present invention seeks to provide an improved system and method to benefits the patient with additional comfort while applying appropriate respiratory therapy to such patient.

SUMMARY OF THE INVENTION

Accordingly, it is an object of one or more embodiments of the present patent application to provide a system for adjusting extrinsic positive end expiratory pressure during an expiratory phase of a ventilator. The ventilator is configured to apply the extrinsic positive end expiratory pressure to a patient during the expiratory phase. The system comprises a computer system that comprises one or more physical processors programmed with computer program instructions which, when executed cause the computer system to: determine a respiratory reactance from airway flow information of the patient and airway pressure information of the patient, the airway flow information and airway pressure information of the patient being obtained from one or more sensors; and continuously adjust the extrinsic positive end expiratory pressure during the expiratory phase of the ventilator such that the determined respiratory reactance falls within a defined respiratory reactance range.

It is yet another aspect of one or more embodiments of the present patent application to provide a method for adjusting extrinsic positive end expiratory pressure during an expiratory phase of a ventilator. The ventilator is configured to apply the extrinsic positive end expiratory pressure to a patient during the expiratory phase. The method is implemented by a computer system that comprises one or more physical processors executing computer program instructions which, when executed, perform the method. The method comprises obtaining, from one or more sensors, airway pressure information of the patient and airway flow information of the patient; determining, by the computer system, a respiratory reactance from the airway flow information of the patient and the airway pressure information of the patient; and continuously adjusting, by the computer system, the extrinsic positive end expiratory pressure during the expiratory phase of the ventilator such that the determined respiratory reactance falls within a defined respiratory reactance range.

It is yet another aspect of one or more embodiments to provide a system for adjusting extrinsic positive end expiratory pressure during an expiratory phase of a ventilator. The ventilator is configured to apply the extrinsic positive end expiratory pressure to a patient during the expiratory phase. The system comprises a means for executing machine-readable instructions with at least one processor. The machine-readable instructions comprises obtaining, from one or more sensors, airway pressure information of the patient and airway flow information of the patient; determining a respiratory reactance from airway flow information of the patient and airway pressure information of the patient; and continuously adjusting, by the computer system, the extrinsic positive end expiratory pressure during the expiratory phase of the ventilator such that the determined respiratory reactance falls within a defined respiratory reactance range.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
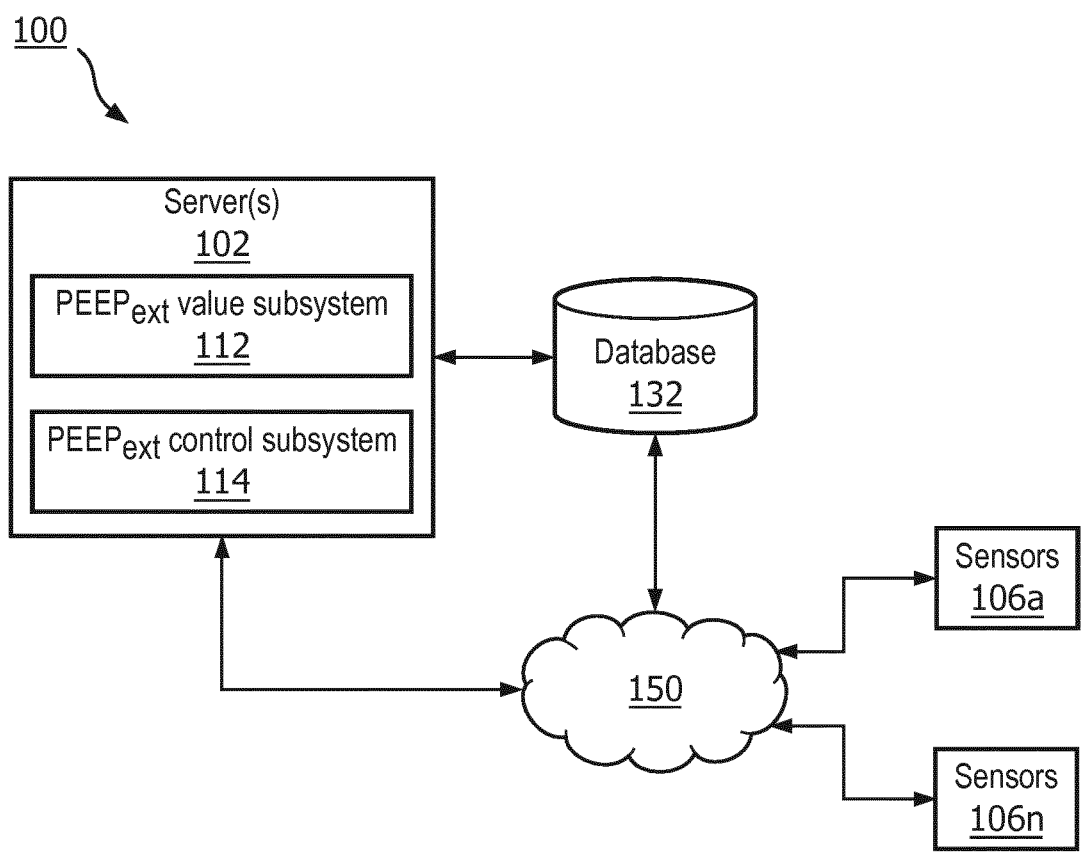
FIG. 1 is an exemplary system for adjusting extrinsic positive end pressure during an expiratory phase of a ventilator in accordance with an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present patent application provides a system 100 for adjusting extrinsic positive end expiratory pressure during an expiratory phase of a ventilator. The ventilator is configured to apply the extrinsic positive end expiratory pressure to a patient during the expiratory phase. As will be clear from the discussions below, in some embodiments, system 100 includes a computer system 102 that has one or more physical processors programmed with computer program instructions which, when executed cause computer system 102 to determine a respiratory reactance from airway flow information of the patient and airway pressure information of the patient; and adjust the extrinsic positive end expiratory pressure during the expiratory phase of the ventilator such that the determined respiratory reactance falls within a defined respiratory reactance range. In an exemplary embodiment this adjustment is done continuously, or essentially continuously. The airway flow information and airway pressure information of the patient are obtained from one or more sensors (106a . . . 106n).

The Positive end-expiratory pressure (PEEP) is the pressure in the lungs (e.g., alveolar pressure) above atmospheric pressure (the pressure outside of the body) that exists at the end of expiration. The extrinsic Positive end-expiratory pressure ($PEEP_{ext}$) is a Positive end-expiratory pressure applied by the ventilator.

In some embodiments, respiratory impedance may be determined using the airway pressure information and the airway flow information. The respiratory impedance (or pulmonary impedance) is a ratio of the Fourier transforms of the airway pressure information and the airway flow information. The real and imaginary parts of the respiratory impedance are the resistance and reactance of the respiratory system, respectively.

In some embodiments, respiratory reactance (or pulmonary reactance) may be determined using the airway pressure information and the airway flow information. For example, an oscillatory flow and pressure delivered to the patient's pulmonary system are used to measure the respiratory impedance. The respiratory reactance, which is the reactance or imaginary component of the respiratory impedance is a useful indicator for the level of the expiratory flow limitation (EFL) that is present in the lungs and, therefore, could be used to appropriately set the level of the $PEEP_{ext}$. A feature of this present patent application is the behavior of the expiratory pressure when used in the ventilator capable of delivering bi-level pressure support.

In some embodiments, system 100 for controlling the ventilator is described where the expiratory pressure adaptively or dynamically changes according to a measurement of the patient's respiratory reactance. For example, the expiratory pressure in the ventilator device is varied at a rate based on analysis of the measured or determined pulmonary reactance. In some embodiments, the expiratory pressure could also be controlled as a function of expiratory flow, guided by the patient's pulmonary reactance. This adaptive control of the expiratory pressure minimizes the EFL, lowers mean airway pressure of the patient and improves patient comfort.

In some embodiments, system 100 is configured to adjust an expiratory waveform based on a function of the respiratory reactance measurement and also adjust an inspiratory pressure amplitude based on a determined pressure support. That is, the present patent application proposes a continuously variable expiratory pressure commensurate to a patient's requirements based on analysis of a patient's respiratory reactance calculated from the airway oscillatory flow information and the airway pressure information delivered to the patient's airways. The method and the system of the present patent application, thus, achieve a balance between optimal therapy and optimal comfort and safety.

Furthermore, since the $PEEP_{ext}$ level starts from a lower pressure, the inspiratory pressure can be lower while still maintaining a therapeutic level of pressure support. This reduction of the inspiratory pressure, and consequently mean airway pressure, further increases patient comfort. Also, the expiratory pressure could dynamically be adjusted based as a function of the expiratory flow. In other words, in the presence of the expiratory flow limitation, as determined by the respiratory reactance, the expiratory pressure would decrease proportionally as the expiratory flow approaches zero as shown in and described with respect to FIG. 3 below.

Figure 2:
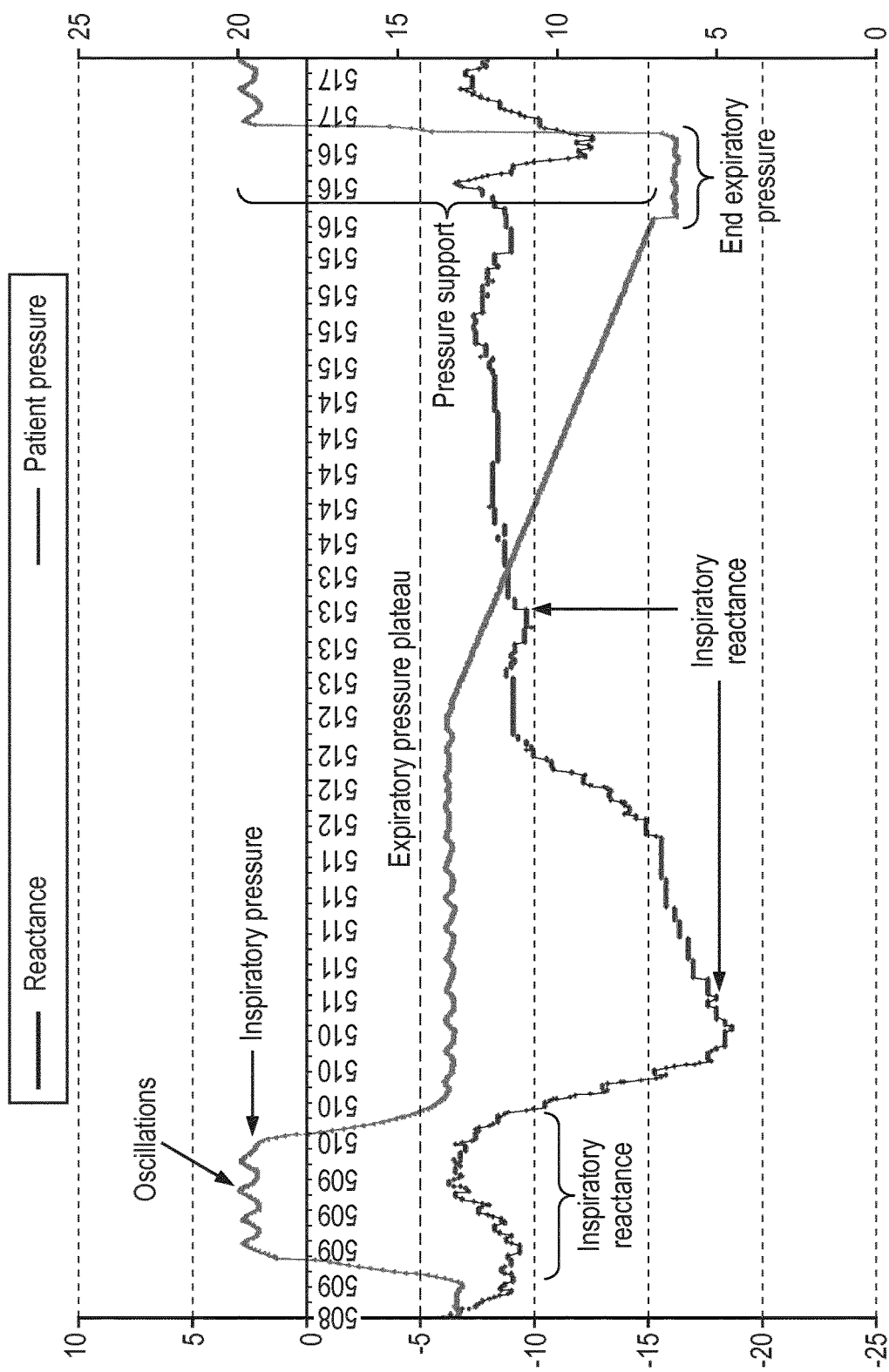
FIG. 2 illustrates expiratory pressure adjusted as a function of respiratory reactance.

FIG. 2 illustrates the behavior of the expiratory pressure in relationship to the respiratory reactance. As can be seen from FIG. 2, the EFL is greatest when the expiratory reactance is most negative in relation to the inspiration reactance up to a certain differential at which point the EFL is minimal and the $PEEP_{ext}$ can be adjusted lower. This typically occurs near mid-point of the expiratory phase when the change in flow begins to decline. The expiratory pressure is maintained at a plateau until a differential between the inspiratory reactance and the expiratory reactance reaches a threshold. The expiratory pressure then begins to decrease until it reaches an end expiratory pressure, just before the start of the inspiratory cycle. The end expiratory pressure could be below the expiratory pressure that was at the start of the expiratory phase or, as FIG. 3 illustrates, the end expiratory pressure could gradually return to the pressure that was at the start of the expiratory phase.

Figure 3:
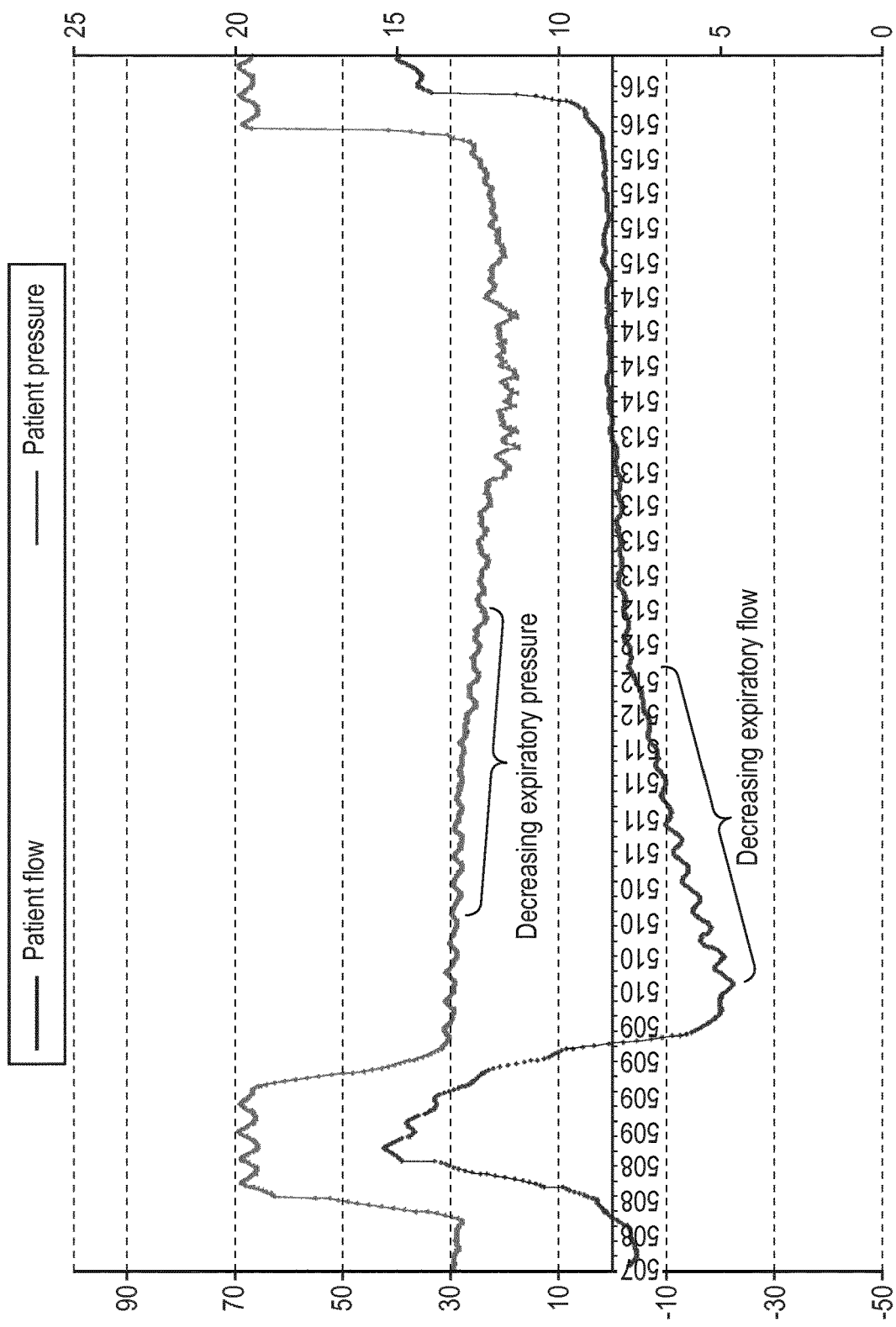
FIG. 3 illustrates expiratory pressure adjusted as a function of expiratory flow.

FIG. 3 illustrates an alternate behavior of the expiratory pressure as a function of the expiratory flow. The expiratory pressure is greatest at the beginning of expiration, but progressively decreases as the expiratory flow begins to approach zero where the ventilatory requirements of the $PEEP_{ext}$ are less, thereby increasing patient comfort without sacrificing therapy. The expiratory pressure then gradually increases. In addition, an expiratory pressure profile that decreases with the expiratory flow delivers a more natural waveform in response to the requirements of a patient's own pulmonary mechanics.

FIG. 1 shows system 100 for adjusting $PEEP_{ext}$ during the expiratory phase of the ventilator, in accordance with one or more embodiments. As shown in FIG. 1, system 100 may comprise server 102 (or multiple servers 102). Server 102 may comprise $PEEP_{ext}$ value subsystem 112, $PEEP_{ext}$ control subsystem 114 or other components or subsystems.

In some embodiments, $PEEP_{ext}$ value subsystem 112 may obtain information associated with a patient's airways. In some embodiments, the information may include airway flow information, airway pressure information, respiratory or airway volume information, or any other airway related information. In some embodiments, the airway flow information of the patient may include information about flow at the airway opening of the patient (e.g., information specifying resistance to airflow at the airway opening during inspiration or expiration, information specifying flow rate at the airway opening during inspiration or expiration, or other information). In some embodiments, the airway pressure information of the patient may include information about pressure at the airway opening of the patient (e.g., information specifying airway pressure at the airway opening during inspiration or expiration or other information). In some embodiments, the airway pressure information of the patient may include information about esophageal pressure (e.g., information specifying airway pressure in the esophagus during inspiration or expiration or other information).

As another example, the information may be obtained from one or more monitoring devices (e.g., airway flow monitoring device, airway pressure monitoring device, airway volume monitoring device or other monitoring devices). In some embodiments, one or more monitoring devices and associated sensors 106a . . . 106n may be configured to monitor respiratory or airway volume. In some embodiments, one or more monitoring devices and associated sensors 106a . . . 106n may be configured to monitor flow at the airway opening. In some embodiments, one or more monitoring devices and associated sensors 106a . . . 106n may be configured to monitor pressure at the airway opening. In some embodiments, one or more monitoring devices and associated sensors 106a . . . 106n may be configured to monitor esophageal pressure. These monitoring devices may include one or more sensors (106a . . . 106n), such as pressure sensors, pressure transducers, flow rate sensors, volume sensors, or other sensors. Sensors (106a . . . 106n) may, for instance, be configured to obtain information of the patient (e.g., airway pressure, airway flow, airway volume, or any other airway parameters) or other information related to the patient's airways.

In one scenario, a monitoring device may obtain information (e.g., based on information from one or more sensors (106a . . . 106n)), and provide information to a computer system (e.g., comprising server 102) over a network (e.g., network 150) for processing. In another scenario, upon obtaining the information, the monitoring device may process the obtained information, and provide processed information to the computer system over a network (e.g., network 150). In yet another scenario, the monitoring device may automatically provide information (e.g., obtained or processed) to the computer system (e.g., comprising server 102).

System 100 also includes a ventilator capable of delivering bi-level pressure support simultaneously with an oscillatory flow and pressure in the frequency range of 2 Hz to 25 Hz and 1-3 $cmH_2O$ peak to peak pressure amplitude.

System 100 is also configured to determine the respiratory impedance and subsequently the reactance or imaginary component of the respiratory impedance (i.e., respiratory reactance) from the oscillatory flow and pressure signals. In some embodiments, $PEEP_{ext}$ value subsystem 112 is configured to determine the respiratory reactance from the obtained airway pressure information of the patient, the obtained airway flow information of the patient, or other airway or airway flow related information. That is, $PEEP_{ext}$ value subsystem 112 is configured to analyze information/data from a device's flow and pressure sensors and calculate or determine respiratory impedance based on the sensor data/information. The respiratory reactance is the imaginary component of the respiratory impedance. $PEEP_{ext}$ value subsystem 112 is configured to extract the respiratory reactance from the determined respiratory impedance. In some embodiments, $PEEP_{ext}$ value subsystem 112 may be configured to determine respiratory reactance directly from the oscillatory flow and pressure signals.

System 100 is also configured to continuously adjust pressure throughout the expiratory phase based on the analysis of the reactance and/or as a function of expiratory flow in order to provide additional comfort while applying appropriate respiratory therapy to the patient. In some embodiments, the pressure profile is adjusted based on the determined or measured reactance measurement. In some embodiments, the flow profile is adjusted based on the determined or measured reactance measurement. In some embodiments, the tidal volume is adjusted based on to the determined or measured reactance measurement.

In some embodiments, system 100 is configured to continuously adjust the extrinsic positive end expiratory pressure during the expiratory phase of the ventilator such that the determined respiratory reactance falls within a defined respiratory reactance range during the entire expiratory phase. In some embodiments, system 100 is configured to continuously adjust the extrinsic positive end expiratory pressure during the expiratory phase of the ventilator such that the determined respiratory reactance mostly falls within a defined respiratory reactance range during the expiratory phase.

In some embodiments, system 100 is configured to continuously adjust the extrinsic positive end expiratory pressure during the expiratory phase of the ventilator such that the determined respiratory reactance falls within a defined respiratory reactance range for at least 30% of the expiratory phase. In some embodiments, system 100 is configured to continuously adjust the extrinsic positive end expiratory pressure during the expiratory phase of the ventilator such that the determined respiratory reactance falls within a defined respiratory reactance range for at least 50% of the expiratory phase. In some embodiments, system 100 is configured to continuously adjust the extrinsic positive end expiratory pressure during the expiratory phase of the ventilator such that the determined respiratory reactance falls within a defined respiratory reactance range for at least 75% of the expiratory phase. In some embodiments, system 100 is configured to continuously adjust the extrinsic positive end expiratory pressure during the expiratory phase of the ventilator such that the determined respiratory reactance falls within a defined respiratory reactance range for at least 90% of the expiratory phase.

In some embodiments, the alteration of the ventilator flow waveform, pressure waveform or tidal volume profile can be a quasi-exponential, can be deterministic or follow a template. The present patent application discloses three different embodiments to continuously adjust the $PEEP_{ext}$ during the expiratory phase.

Figure 4:
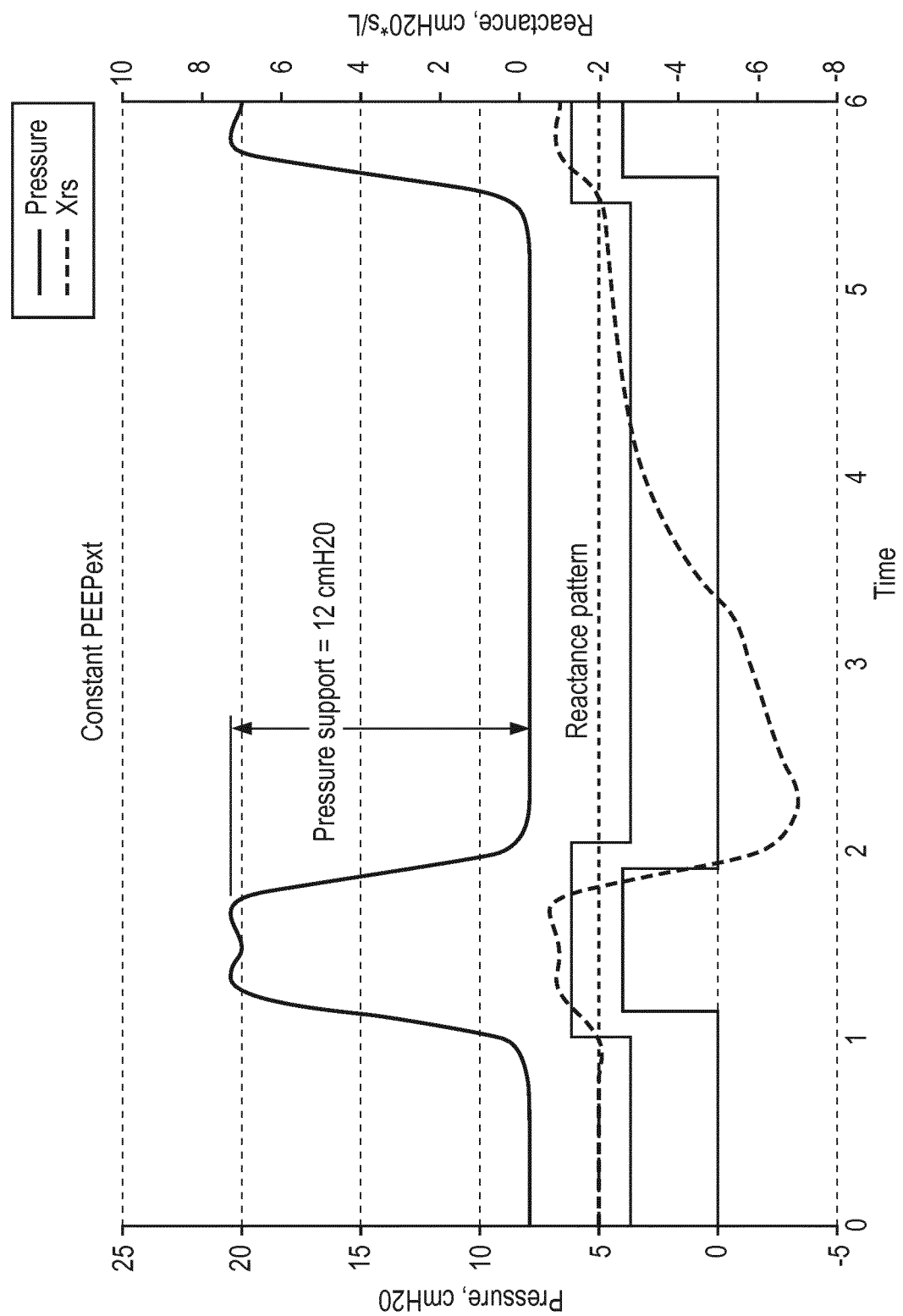
FIG. 4 shows a graphical illustration of the $PEEP_{ext}$ being maintained constant during the expiratory phase in accordance with the prior art.

In the prior art method (e.g., as shown in FIG. 4) where the $PEEP_{ext}$ is constant during the expiration phase, the constant $PEEP_{ext}$ (applied during the expiration phase) was updated on a breath-by-breath basis. By contrast, the $PEEP_{ext}$ is continuously adjusted on a sample-by-sample basis in the embodiments of the present patent application.

The first embodiment to continuously adjust the $PEEP_{ext}$ during the expiratory phase is a feedback control. That is, the respiratory reactance value, $X_{rs}$ is fed back to continuously adjust the $PEEP_{ext}$ during the expiratory phase. A sample rate of 100 Hz is used in this embodiment. For example, the method and the system of the present patent application continuously adjusts the $PEEP_{ext}$ during the expiratory phase using the Equation (2) below.

$$PEEP_{ext}(k) = PEEP_{ext}(k-1) + \text{error term derived from reactance}(X_{rs}) \qquad (2)$$

where $PEEP_{ext}$ is the extrinsic positive end expiratory pressure, and k is the sample index.

In some embodiments, the error term or value is derived by comparing the determined or measured respiratory reactance with a defined respiratory reactance range. In some embodiments, the error term or value includes the difference between the determined or measured respiratory reactance and the defined respiratory reactance range, if the determined or measured respiratory reactance falls outside the defined respiratory reactance range.

Figure 6:
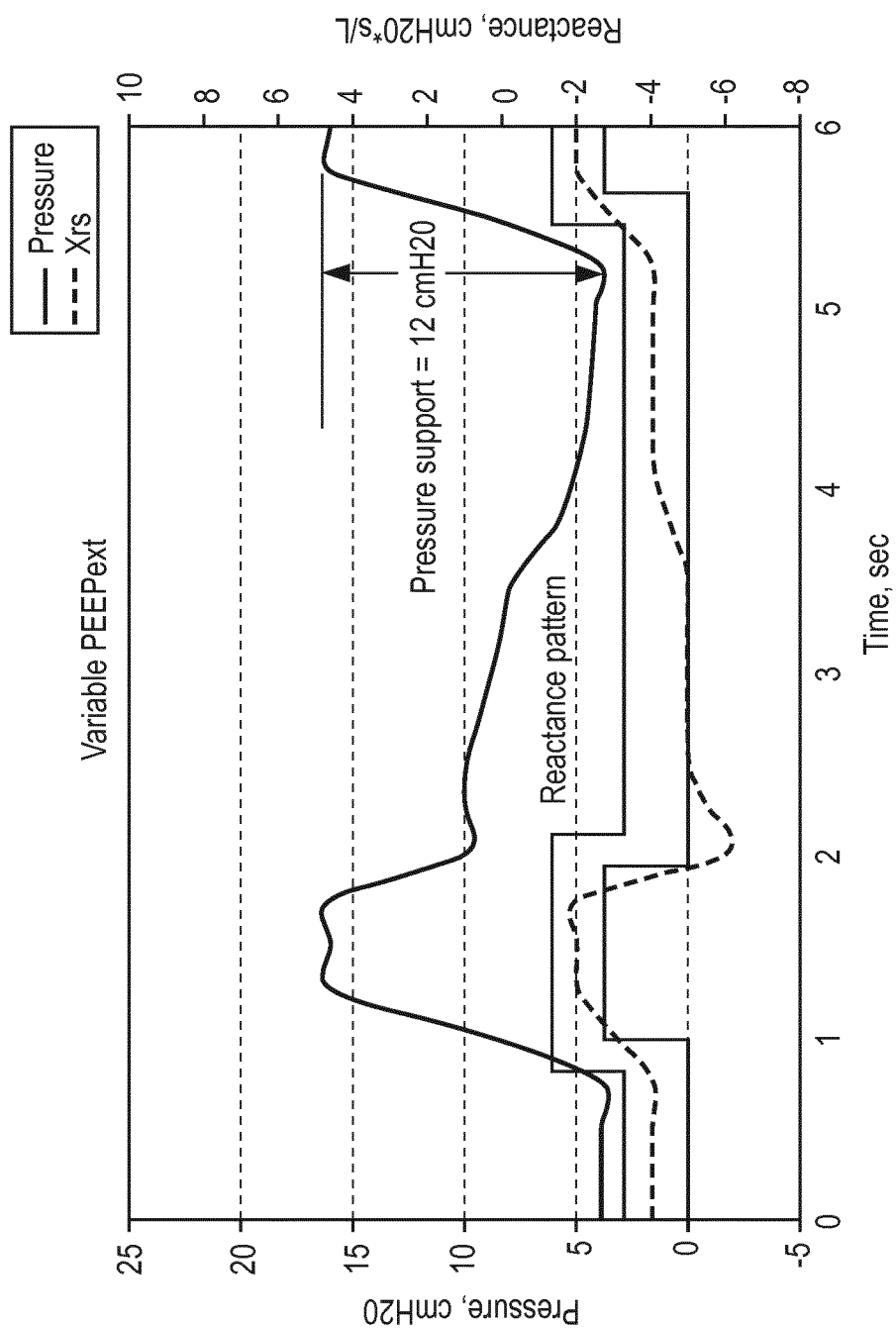
FIG. 6 shows a graphical illustration of the variable $PEEP_{ext}$ being used during the expiratory phase in accordance with an embodiment of the present patent application.

In some embodiments, the desired or defined respiratory reactance range includes values of the reactance (during the expiratory phase) between −1 and −7 $cmH_2O*s/L$. The defined respiratory reactance range is shown in FIG. 6. For example, the box labelled "Reactance Pattern" in FIG. 6 is the defined respiratory reactance range. In some embodiments, as shown in FIG. 6, the lower limit of the defined respiratory reactance range is −5 $cmH_2O*s/L$ and the upper limit of the defined respiratory reactance range is −3 $cmH_2O*s/L$. In some embodiments, the limits or values of the defined respiratory reactance range as described and shown here, are up to 5 percent greater than or up to 5 percent less than those described above. In some embodiments, the limits or values of the defined respiratory reactance range as described here, are up to 10 percent greater than or up to 10 percent less than those described above. In some embodiments, the limits or values of the defined respiratory reactance range as described here, are up to 15 percent greater than or up to 15 percent less than those described above. In some embodiments, the limits or values of the defined respiratory reactance range as described here, are up to 20 percent greater than or up to 20 percent less than those described above.

In some embodiments, the defined reactance range may be obtained by clinical testing. In some embodiments, the defined reactance range may be obtained using data analytics. In some embodiments, the defined reactance range may be obtained from research publications.

In some embodiments, the defined respiratory reactance range may be referred to as a specified respiratory reactance range. In some embodiments, the specified respiratory reactance range may be specified by the patient or a caregiver.

In some embodiments, the defined respiratory reactance range may be referred to as a predetermined respiratory reactance range. In some embodiments, the predetermined respiratory reactance range is determined by: determining, by the computer system, the defined respiratory reactance range using previously obtained airway pressure information a plurality of patients, previously obtained airway flow information from the plurality of patients, and/or previously determined respiratory reactance information; continuously obtaining, by the computer system, subsequent airway pressure information of the plurality of patients, subsequent airway flow information of the plurality of patients, and/or subsequent respiratory reactance information; and continuously modifying, by the computer system, the defined respiratory reactance range based on the subsequent airway pressure information, the subsequent airway flow information, and/or the subsequent respiratory reactance information.

In some embodiments, a subsystem of system 100 may be configured to determine the defined reactance range using previously obtained airway pressure information, previously obtained airway flow information, and/or previously obtained expiratory reactance information from a plurality of patients. In some embodiments, this subsystem is also configured to continuously obtain subsequent airway pressure information, subsequent airway flow information and/or subsequent expiratory reactance information of the plurality of patients. That is, the subsystem may continuously obtain subsequent information associated with the multiple patients. As an example, the subsequent information may comprise additional information corresponding to a subsequent time (after a time corresponding to information that was used to determine the respiratory reactance). As an example, the subsequent information may be obtained from one or more monitoring devices and associated one or more sensors. The subsequent information may be utilized to further update or modify the defined reactance range (e.g., new information may be used to dynamically update or modify the defined reactance range), etc. In some embodiments, this subsystem is configured to then continuously modify or update the defined reactance range based on the subsequent airway pressure information, the subsequent airway flow information, the subsequent expiratory reactance information or other subsequent information.

For example, the subsequent information may also be configured to provide further input on setting the $PEEP_{ext}$ such as minimum and maximum values that could be constant or variable during the expiratory phase.

In some embodiments, the defined respiratory reactance pattern may be dynamically updated, modified, or adjusted by algorithms or machine learning using information/data collected from, for example, sleep monitors, photoplethysmography, activity sensors, voice and video analysis and questionnaires on mood and quality of life metrics.

In some embodiments, the defined reactance range may be saved into a database (e.g., database 132) and retrieved from the database as needed. As described above, the subsystem of system 100 may continuously update/modify the defined reactance range.

The second embodiment to continuously adjust the $PEEP_{ext}$ during the expiratory phase is an adaptive feed-forward compensation or control (AFPEEP). Current values of patient flow and tidal volume are used as inputs to the AFPEEP.

Adaptive feed-feedforward control is well understood by a person skilled in the art and the present patent application does not limit itself to any one specific adaptive feed-feedforward method. For example, the method and the system of the present patent application continuously adjusts the $PEEP_{ext}$ during the expiratory phase using Equation (3) below. For example, Equation (3) is a three parameter adaptive feed-feedforward control used to calculate the PEEPext.

$$PEEP_{ext}(k)=Po+A*Flow(k)+B*Vt(k) \quad (3)$$

where $PEEP_{ext}$ is the extrinsic positive end expiratory pressure;
Po is a constant pressure value;
A is the first coefficient;
B is the second coefficient;
Flow is the current airway flow value of the patient;
Vt is the current tidal volume value of the patient; and
k is the sample index.

A continuous time version of Equation (3) may be readily obtainable and obvious to a person skilled in the art. The values of Po, A and B are adjusted such that the respiratory reactance, $X_{rs}$ falls within the defined reactance range. In some embodiments, the $PEEP_{ext}$ is constrained between minimum and maximum values.

Figure 5:
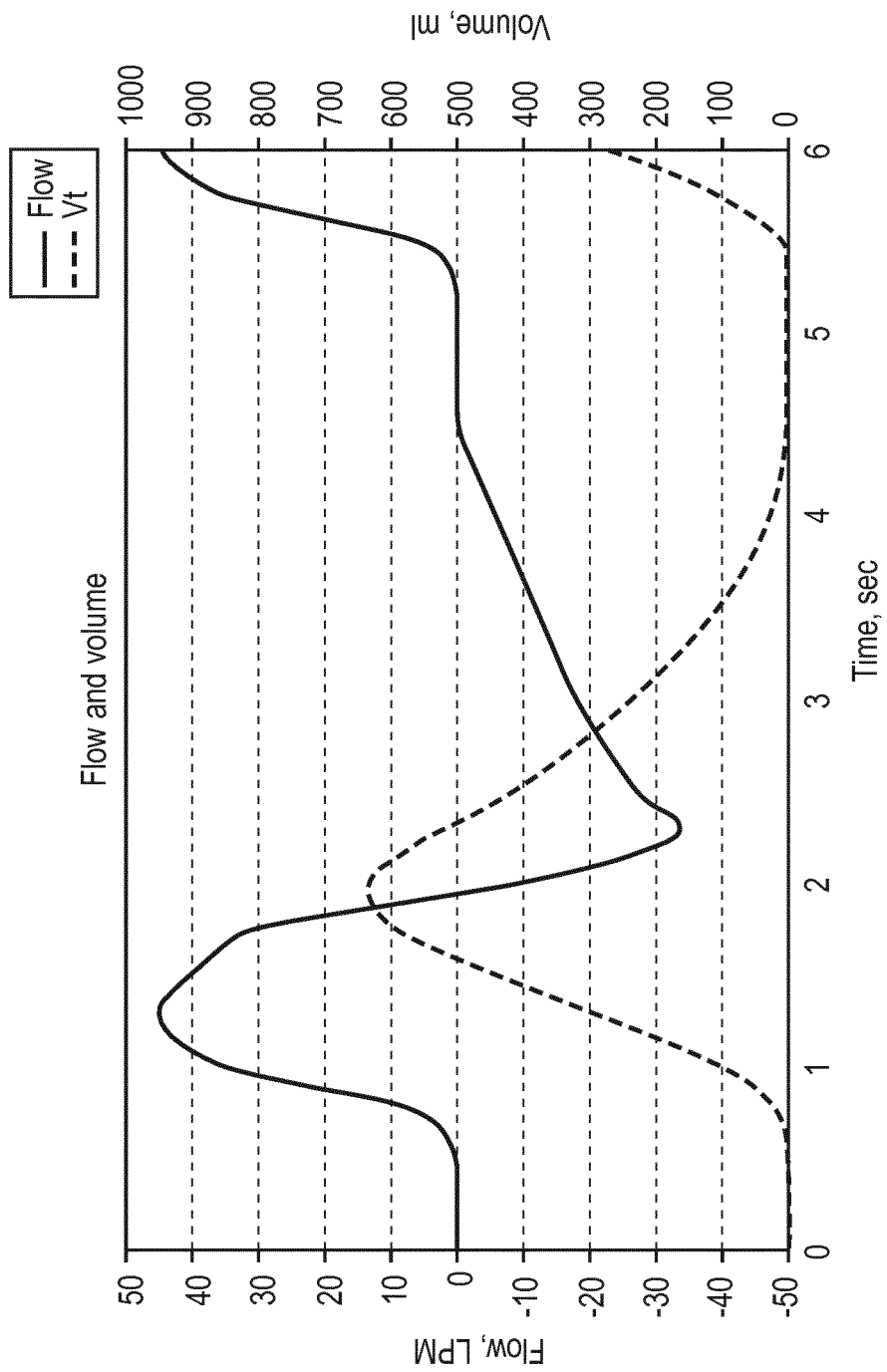
FIG. 5 shows a graphical illustration of flow and tidal volume measurements being used to generate the variable $PEEP_{ext}$ during the expiratory phase in accordance with an embodiment of the present patent application.

FIG. 5 shows current airway flow values and the current tidal volume values of the patient. FIG. 5 shows airway flow on the left hand side Y-axis of the graph, which is measured in Liters/min, L/min or L/m; tidal volume on the right hand side Y-axis of the graph, which is measured in milliliters; and time on the X-axis of the graph, which is measured in seconds.

The airway flow values and the tidal volume values of the patient shown in FIG. 5 are used in Equation (3) above to obtain $PEEP_{ext}(k)$. $PEEP_{ext}(k)$ thus generated is shown in the graph in FIG. 6.

The third embodiment to continuously adjust the $PEEP_{ext}$ during the expiratory phase is to use both feedback control and adaptive feed-forward control. For example, the $PEEP_{ext}$ is calculated using the Equation (4) below.

$$PEEP_{ext}(k)=F\{Po,Flow,Vt,PEEP_{ext}\} \quad (4)$$

where $PEEP_{ext}$ is the extrinsic positive end expiratory pressure;
F{ } is a function;
Po is a constant pressure value;
Flow is the current airway flow value of the patient;
Vt is the current tidal volume value of the patient; and
k is the sample index.

FIG. 6 shows a graphical illustration of the $PEEP_{ext}$ being variable (e.g., adaptively or continuously adjusted) during the expiratory phase in accordance with an embodiment of the present patent application. FIG. 6 shows patient pressure on the left hand side Y-axis of the graph. For example, the patient pressure is measured at a patient interface (e.g., a mask) and is measured in units of $cmH_2O$. FIG. 6 shows respiratory reactance on the right hand side Y-axis of the graph, which is measured in $cmH_2O*s/L$. FIG. 6 shows time on the X-axis of the graph, which is measured in seconds. The top graph in FIG. 6 is an illustration of the patient pressure information and the bottom graph in FIG. 6 is an illustration of the respiratory impedance or respiratory reactance.

$PEEP_{ext}$ delivered to the patient is continuously adjusted such that the reactance Xrs is within the defined reactance range (e.g., the box labelled "Reactance Pattern" in FIG. 6).

As shown in FIG. 6, a better $PEEP_{ext}$ waveform would be high during the initial phases of the expiration and would trend to lower pressure towards the end of expiration. For example, the pressure support is maintained but is at a lower peak inspiratory pressure than that of FIG. 4.

In some embodiments, the various computers and subsystems illustrated in FIG. 1 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112 and 114 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112 and 114 described herein is for illustrative purposes, and is not intended to be limiting, as any of subsystems 112 and 114 may provide more or less functionality than is described. For example, one or more of subsystems 112 and 114 may be eliminated, and some or all of its functionality may be provided by other ones of subsystems 112 and 114. As another example, additional subsystems may be programmed to perform some or all of the functionality attributed herein to one of subsystems 112 and 114.

Figure 7:
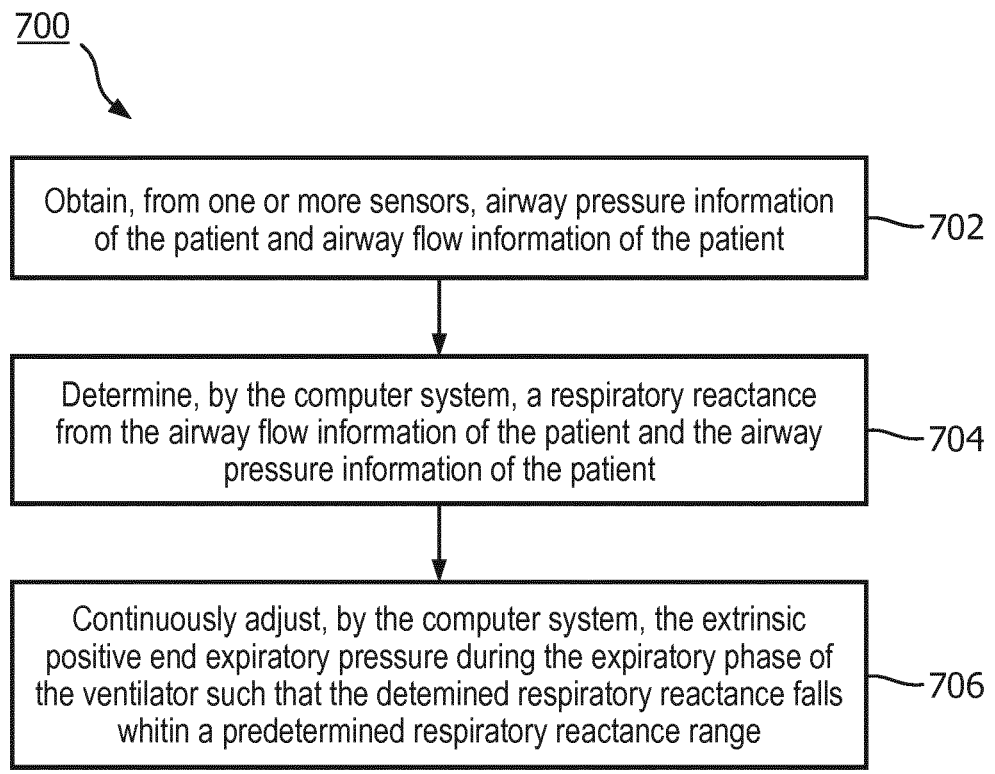
FIG. 7 shows a method for adjusting extrinsic positive end pressure during the expiratory phase of the ventilator in accordance with an embodiment of the present patent application.

FIG. 7 is a flow chart for adjusting extrinsic positive end expiratory pressure during an expiratory phase of a ventilator, the ventilator being configured to apply the extrinsic positive end expiratory pressure to a patient during the expiratory phase. Referring to FIG. 7, a method 700 for adjusting the extrinsic positive end expiratory pressure during the expiratory phase of the ventilator is provided. Method 700 is implemented by computer system 102 that comprises one or more physical processors executing computer program instructions which, when executed, perform method 700. Method 700 comprises: obtaining, from one or more sensors (106a . . . 106n), airway pressure information of the patient and airway flow information of the patient at procedure 702; determining, by computer system 102, a respiratory reactance from the airway flow information of the patient and the airway pressure information of the patient at procedure 704; and continuously adjusting, by computer system 102, the extrinsic positive end expiratory pressure during the expiratory phase of the ventilator such that the determined respiratory reactance falls within a defined respiratory reactance range at procedure 706.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system for adjusting extrinsic positive end expiratory pressure during an expiratory phase of a ventilator, the ventilator being configured to apply the extrinsic positive end expiratory pressure to a patient during the expiratory phase, the system comprising:
a computer system that comprises one or more physical processors programmed with computer program instructions which, when executed cause the computer system to:
determine a respiratory reactance from airway flow information of the patient and airway pressure information of the patient, the airway flow information and airway pressure information of the patient being obtained from one or more sensors; and
adjust the extrinsic positive end expiratory pressure during the expiratory phase of the ventilator such that the determined respiratory reactance falls within a defined respiratory reactance range.

2. The system of claim 1, wherein the computer system adjusts the extrinsic positive end expiratory pressure based on an adaptive feed forward signal generated by the computer system, wherein the adaptive feed forward signal is generated such that the determined respiratory reactance falls within the defined respiratory reactance range.

3. The system of claim 1, wherein the computer system adjusts the extrinsic positive end expiratory pressure by adjusting a constant pressure value, a first coefficient and a second coefficient such that the determined respiratory reactance falls within the defined respiratory reactance range in accordance with the following equation:

$$PEEP_{ext}(k)=Po+A*Flow(k)+B*Vt(k)$$

$PEEP_{ext}$ is the extrinsic positive end expiratory pressure;
Po is a constant pressure value;
Flow is the current airway flow value of the patient;
A is the first coefficient;
Vt is the current tidal volume value of the patient;
B is the second coefficient; and
k is the sample index.

4. The system of claim 1, wherein the computer system adjusts the extrinsic positive end expiratory pressure based on a feedback signal generated by the computer system, wherein the feedback signal is generated such that the determined respiratory reactance falls within the defined respiratory reactance range.

5. The system of claim 1, wherein the defined respiratory reactance range is determined by:
   determining, by the computer system, the defined respiratory reactance range using previously obtained airway pressure information from a plurality of patients, previously obtained airway flow information from the plurality of patients, and/or previously determined respiratory reactance information;
   obtaining, by the computer system, subsequent airway pressure information of the plurality of patients, subsequent airway flow information of the plurality of patients, and/or subsequent respiratory reactance information; and
   modifying, by the computer system, the defined respiratory reactance range based on the subsequent airway pressure information, the subsequent airway flow information, and/or the subsequent respiratory reactance information.

6. A method for adjusting extrinsic positive end expiratory pressure during an expiratory phase of a ventilator, the ventilator being configured to apply the extrinsic positive end expiratory pressure to a patient during the expiratory phase, the method being implemented by a computer system that comprises one or more physical processors executing computer program instructions which, when executed, perform the method, the method comprising:
   obtaining, from one or more sensors, airway pressure information of the patient and airway flow information of the patient;
   determining, by the computer system, a respiratory reactance from the airway flow information of the patient and the airway pressure information of the patient; and
   adjusting, by the computer system, the extrinsic positive end expiratory pressure during the expiratory phase of the ventilator such that the determined respiratory reactance falls within a defined respiratory reactance range.

7. The method of claim 6, wherein the extrinsic positive end expiratory pressure during the expiratory phase of the ventilator is continuously adjusted based on an adaptive feed forward signal generated by the computer system, wherein the adaptive feed forward signal is generated such that the determined respiratory reactance falls within the defined respiratory reactance range.

8. The method of claim 6, wherein the extrinsic positive end expiratory pressure during the expiratory phase of the ventilator is adjusted by adjusting a constant pressure value, a first coefficient and a second coefficient such that the determined respiratory reactance falls within the defined respiratory reactance range in accordance with the following equation:

$$PEEP_{ext}(k)=Po+A*Flow(k)+B*Vt(k)$$

$PEEP_{ext}$ is the extrinsic positive end expiratory pressure;
Po is a constant pressure value;
Flow is the current airway flow value of the patient;
A is the first coefficient;
Vt is the current tidal volume value of the patient;
B is the second coefficient; and
k is the sample index.

9. The method of claim 6, wherein the extrinsic positive end expiratory pressure during the expiratory phase of the ventilator is adjusted based on a feedback signal generated by the computer system, wherein the feedback signal is generated such that the determined respiratory reactance falls within the defined respiratory reactance range.

10. The method of claim 6, wherein the defined respiratory reactance range is determined by:
    determining, by the computer system, the defined respiratory reactance range using previously obtained airway pressure information from a plurality of patients, previously obtained airway flow information from the plurality of patients, and/or previously determined respiratory reactance information;
    obtaining, by the computer system, subsequent airway pressure information of the plurality of patients, subsequent airway flow information of the plurality of patients, and/or subsequent respiratory reactance information; and
    modifying, by the computer system, the defined respiratory reactance range based on the subsequent airway pressure information, the subsequent airway flow information, and/or the subsequent respiratory reactance information.

11. A system for adjusting extrinsic positive end expiratory pressure during an expiratory phase of a ventilator, the ventilator being configured to apply the extrinsic positive end expiratory pressure to a patient during the expiratory phase, the system comprising:
    a means for executing machine-readable instructions with at least one processor, wherein the machine-readable instructions comprising:
    obtaining, from one or more sensors, airway pressure information of the patient and airway flow information of the patient;
    determining a respiratory reactance from airway flow information of the patient and airway pressure information of the patient; and
    adjusting, by the computer system, the extrinsic positive end expiratory pressure during the expiratory phase of the ventilator such that the determined respiratory reactance falls within a defined respiratory reactance range.

12. The system of claim 11, wherein the extrinsic positive end expiratory pressure during the expiratory phase of the ventilator is adjusted based on an adaptive feed forward signal generated by the computer system, wherein the adaptive feed forward signal is generated such that the determined respiratory reactance falls within the defined respiratory reactance range.

13. The system of claim 11, wherein the extrinsic positive end expiratory pressure during the expiratory phase of the ventilator is adjusted by adjusting a constant pressure value, a first coefficient and a second coefficient such that the determined respiratory reactance falls within the defined respiratory reactance range in accordance with the following equation:

$$PEEP_{ext}(k)=Po+A*Flow(k)+B*Vt(k)$$

$PEEP_{ext}$ is the extrinsic positive end expiratory pressure;
Po is a constant pressure value;
Flow is the current airway flow value of the patient;
A is the first coefficient;
Vt is the current tidal volume value of the patient;
B is the second coefficient; and
k is the sample index.

14. The system of claim 11, wherein the extrinsic positive end expiratory pressure during the expiratory phase of the ventilator is adjusted based on a feedback signal generated by the computer system, wherein the feedback signal is generated such that the determined respiratory reactance falls within the defined respiratory reactance range.

15. The system of claim 11, wherein the defined respiratory reactance range is determined by:
  determining, by the computer system, the defined respiratory reactance range using previously obtained airway pressure information from a plurality of patients, previously obtained airway flow information from the plurality of patients, and/or previously determined respiratory reactance information;
  obtaining, by the computer system, subsequent airway pressure information of the plurality of patients, subsequent airway flow information of the plurality of patients, and/or subsequent respiratory reactance information; and
  modifying, by the computer system, the defined respiratory reactance range based on the subsequent airway pressure information, the subsequent airway flow information, and/or the subsequent respiratory reactance information.

* * * * *